(12) United States Patent
McManus

(10) Patent No.: US 9,250,175 B1
(45) Date of Patent: Feb. 2, 2016

(54) OPTICAL MULTI-PASS CELL FOR LONG PATH-LENGTH SPECTROSCOPY

(71) Applicant: Aerodyne Research, Inc., Billerica, MA (US)

(72) Inventor: J. Barry McManus, Arlington, MA (US)

(73) Assignee: AERODYNE RESEARCH, INC., Billerica, MA (US)

(*) Notice: Subject to any disclaimer, the term of this patent is extended or adjusted under 35 U.S.C. 154(b) by 0 days.

(21) Appl. No.: 14/572,702

(22) Filed: Dec. 16, 2014

(51) Int. Cl.
*G01N 21/03* (2006.01)
*G01J 3/02* (2006.01)

(52) U.S. Cl.
CPC .............. *G01N 21/031* (2013.01); *G01J 3/021* (2013.01); *G01N 2201/068* (2013.01)

(58) Field of Classification Search
CPC ............ G01N 21/3504; G01N 21/031; G01N 21/0303; G01N 30/72; G01N 2201/0668; G01J 3/42
USPC .......... 356/244, 246, 432–440, 319, 326, 413
See application file for complete search history.

(56) References Cited

U.S. PATENT DOCUMENTS

| | | | |
|---|---|---|---|
| 3,437,954 A | 4/1969 | Herriott et al. | |
| 3,550,039 A | 12/1970 | Herriott | |
| 5,485,276 A | 1/1996 | Bien et al. | |
| 7,307,716 B2 | 12/2007 | Silver | |
| 8,842,282 B2* | 9/2014 | Keller | G01N 21/3504 356/326 |
| 2006/0158644 A1* | 7/2006 | Silver | G01N 21/05 356/246 |
| 2006/0232772 A1* | 10/2006 | Silver | G01N 21/05 356/246 |
| 2013/0003045 A1* | 1/2013 | Wilkins | G01J 3/42 356/51 |
| 2013/0293882 A1* | 11/2013 | Dottery | G01J 3/44 356/301 |
| 2014/0160474 A1* | 6/2014 | Keller | G01N 21/3504 356/246 |
| 2015/0192468 A1* | 7/2015 | Pearman | H04B 15/00 356/451 |
| 2015/0260695 A1* | 9/2015 | Spartz | G01N 30/74 250/339.01 |

OTHER PUBLICATIONS

Blows, J.L., et al., "Mode Characteristics of Twisted Resonators Composed of Two Cylindrical Mirrors," *Optics Express*, vol. 2, No. 5, Mar. 2, 1998, pp. 184-190.

Borysow, Jacek, et al. "Laser multipass system with interior cell configuration," *Applied Optics* vol. 50, No. 30, Oct. 20, 2011, pp. 5812-5815.

Dyroff, C. et al., "A Multipass Cell Design for Stark-Modulation Spectroscopy," *Applied Optics*, vol. 46, Issue 19, Jul. 1, 2007, (26 pages).

(Continued)

*Primary Examiner* — Hoa Pham
(74) *Attorney, Agent, or Firm* — Cesari and McKenna, LLP; James A. Blanchette

(57) ABSTRACT

In one embodiment, an improved multi-pass cell for a long path-length spectrometer is designed to include a perturbing mirror that causes a base pattern of reflections to be repeated multiple times, where each subsequent base pattern of reflections is rotated about the axis at an angle from a prior base pattern, to circulate the base patters about the cell. The base pattern may be a Herriott cell pattern. The improved multi-pass cell may be constructed with a concave front mirror centered along an axis of the cell, and a concave back mirror centered along the axis and facing the front mirror. The perturbing mirror may be centered along the axis, facing the front mirror and located at a perturbing mirror spacing in front of the back mirror or behind the back mirror, depending on the implementation.

20 Claims, 9 Drawing Sheets

(56) References Cited

OTHER PUBLICATIONS

Engel, G.S., et al., "Precise Multipass Herriott Cell Design: Derivation of controlling design equations," *Optics Letters*, vol. 32, No. 6, Mar. 15, 2007, pp. 704-706.
Grassi, L. et al., "Theoretical and Practical Consideration of the Construction of a Zero-Geometric-loss Multiple-Pass Cell Based on the Use of Monolithic Multiple-Face Retroreflectors," *Applied Optics*, vol. 40, No. 33, Nov. 20, 2001, pp. 6062-6071.
Hu, T. A., et al. "Improved multipass optics for diode laser spectroscopy." *Review of scientific instruments*, vol. 64, No. 12, Dec. 1993, pp. 3380-3383.
Kasyutich, V.L. et al., "Multipass optical cell based upon two cylindrical mirrors for tunable diode laser absorption spectroscopy." *Applied Physics*, B 88, vol. 1, Jun. 1, 2007, pp. 125-130.
McManus, J.B. et al., "Astigmatic Mirror Multipass Absorption Cells for Long-Path-Length Spectroscopy," *Applied Optics*, vol. 34, No. 18, Jun. 20, 1995, pp. 3336-3348.
McManus, J. Barry. "Paraxial matrix description of astigmatic and cylindrical mirror resonators with twisted axes for laser spectroscopy," *Applied Optics*, vol. 46, No. 4, Feb. 1, 2007, pp. 472-482.
McManus, J.B. et al., "Dual Quantum Cascade Laser Trace Gas Instrument with Astigmatic Herriott Cell at High Pass Number," *Applied Optics*, vol. 50, No. 4, Feb. 1, 2011, pp. A1-A13.
Riedel, Jens, et al. "A simple yet effective multipass reflector for vibrational excitation in molecular beams." *Review of Scientific Instruments*, vol. 79, No. 3, Mar. 2008 (4 pages).
Robert, Claude, "Simple, stable, and compact multiple-reflection optical cell for very long optical paths," *Applied Optics* vol. 46, No. 22, Aug. 1, 2007, pp. 5408-5418.
Röpcke, J., et al. "Application of mid-infrared tuneable diode laser absorption spectroscopy to plasma diagnostics: a review." *Plasma Sources Science and Technology*, vol. 15, No. 4, Nov. 2006, pp. S148-S168.
Sennaroglu, A. et al., "Design criteria for Herriott-type multi-pass cavities for ultrashort pulse lasers." *Optics Express*, vol. 11, No. 9, May 5, 2003, pp. 1106-1113.
Silver, Joel A. "Simple dense-pattern optical multipass cells." *Applied optics* vol. 44, No. 31, Nov. 1, 2005, pp. 6545-6556.
Tarsitano, C.G. et al., "Multilaser Herriott cell for planetary tunable laser spectrometers," *Applied Optics*, vol. 46, No. 28, Oct. 2007, pp. 6923-6935.
Tittel, F.K., et al. "Mid-infrared laser applications in spectroscopy." *Solid-State Mid-Infrared Laser Sources*, Springer Berlin Heidelberg, Jun. 13, 2003, pp. 445-516.
Werle, Peter, "A Review of Recent Advances in Semiconductor Laser Based Gas Monitors," *Spectrochimica Acta*, Part A vol. 54, Feb. 1, 1998, pp. 197-236.

* cited by examiner

OPTICAL MULTI-PASS CELL FOR LONG PATH-LENGTH SPECTROSCOPY

BACKGROUND

1. Technical Field

The present disclosure relates generally to spectrometers, and more specifically to optical multi-pass cells for use in long path-length spectrometers.

2. Background Information

Long path-length spectrometers may be used to make highly sensitive and precise measurements of a wide variety of gaseous molecules. In a basic configuration, a long path length spectrometer includes a light source (e.g., a laser), a multi-pass cell and a detector. The light source directs a beam into the multi-pass cell, in which a gaseous sample is disposed. The beam is repeatedly reflected within the multi-pass cell, where it may interact with the gaseous sample and be partially absorbed. By repeatedly reflecting the beam, the multi-pass cell increases the optical path length through the gaseous sample, thereby increasing absorption. A remaining portion of the beam emerges from the multi-pass cell and is detected by the light detector. A computer system may control the light source to change the wavelength or other characteristics of the beam, and receive and analyze signals from the light detector. To measure an absorption line for a gaseous molecule, the computer system may cause the light source to linearly scan over the line, and use the light detector to observe the direct absorption shape, or it may cause the light source to sinusoidally modulate, and analyze the signal from the light detector in terms of harmonic content. In practice, the configuration of long path-length spectrometers tends to be more complicated than this basic example, including other features such as multiple light sources (e.g., lasers), a reference cell, a power-nominalization path, etc. However, the general principles are similar.

For some measurement problems, for example where concentrations of the gaseous molecule are low and/or line strength is weak, the use of a multi-pass cell may be key to achieving desired detection limits. A variety of different types of multi-pass cells have been deployed over the years, including White cells, Herriott cells, and Astigmatic Herriott cells, among others. While the specific operation of these cells differs, they each produce a series of reflections between opposing mirrors that may be characterized as a spot pattern on the mirrors (herein sometimes referred to simply as the "pattern"). In each of these types of multi-pass cells, a beam enters the multi-pass cell, circulates about the cell for a definite number of reflections according to the pattern, and then exits the cell. The mirrors may serve to repeatedly refocus the beam to keep it from spreading indefinitely.

White cells were the first multi-pass cells to be widely used in spectroscopy. FIG. 1 is diagram depicting an example White cell 100. The example White cell 100 includes a concave front mirror 110, and a concave split back mirror 120 consisting of two halves that are disposed at an inward tilt. The front mirror 110 and split back mirror 120 generally have the same radius of curvature. A beam 150 from a light source (e.g., a laser) (not shown) is directed onto a back mirror half 140, and repeatedly reflected between the back mirror 120 and the front mirror 110 according to a known pattern (the "White cell pattern"), before eventually exiting the White cell 100. The tilt of the back mirror halves 130, 140 may be used to adjust the number of reflections. The White cell pattern typically includes a double row of tightly focused spots on the front mirror and two sets of large overlapping spots on the back mirror.

The Herriott cell is a newer, somewhat simpler design than the White cell, that does not require a split mirror. FIG. 2 is a diagram depicting an example Herriott cell 200. The example Herriott cell 200 includes a concave front mirror 210, and a concave back mirror 220. A beam 230 from the light source (not shown) enters the Herriott cell 200 through a coupling hole 240 in the front mirror 210 at an angle, and repeatedly reflects between the back mirror 220 and the front mirror 210 according to a known pattern (the "Herriott cell pattern"), before eventually exiting the through the coupling hole 240. Typically the beam circulates with a fixed angular advance per reflection, such that the Herriott cell pattern includes an elliptical (or sometimes circular) series of spots on the front mirror 210 and back mirrors 220. The number of reflections may be changed by changing the spacing between the front mirror 210 and the back mirror 220.

In one variant of a Herriott cell, referred to as an astigmatic Herriott cell, the front mirror and the back mirror each have two different radii of curvature (e.g., have a toric surface). The astigmatic Herriott cell produces a pattern of spots which nearly fills in the area of circular mirrors (essentially a Lissajuos pattern). The number of reflections may be changed by a combination of mirror twist and spacing between the front mirror and back mirror.

While existing multi-pass cells, such as White cells, Herriott cells and Astigmatic Herriott cells, have been used successfully to conduct innumerable measurements, there are areas in which their performance may be further improved. For example, some existing multi-pass cells (e.g., astigmatic Herriott cells) utilize mirrors whose surfaces are complex and thereby expensive to produce. Similarly, some existing multi-pass cells have lower than desired optical throughput, while others may have patterns that do not fully fill the available surface area of the mirrors, resulting an inefficient use of the cell's volume. Further, some existing multi-pass cells do not provide a simple mechanism for adjusting the number of reflections.

Accordingly, there is a need for an improved multi-pass cell for long path-length spectrometers that may address some or all of these shortcomings.

SUMMARY

In one embodiment, an improved multi-pass cell for a long path-length spectrometer includes a perturbing mirror that causes a base pattern of reflections (e.g., a Herriott cell pattern) to be repeated multiple times, where each subsequent base pattern is rotated about an axis of the cell at an angle from a prior base pattern. By circulating the base pattern multiple times, the number of reflections of the base pattern is effectively multiplied by a pattern multiplication factor.

More specifically, in one embodiment, an improved multi-pass cell may include a concave front mirror opposing a concave back mirror of equal diameter, each centered along the axis of the cell. A perturbing mirror having a smaller diameter may be centered along the axis facing the front mirror, separated from the back mirror by a perturbing mirror spacing that is generally significantly less than a spacing between the front mirror and the back mirror. In some implementations, the perturbing mirror may be located in front of the back mirror relative to the front mirror. In such implementations, the perturbing mirror may have a convex curvature. In other implementations, the perturbing mirror may be located behind the back mirror, with the back mirror having a hole therein to allow the beam to reach the perturbing mirror. In such implementations, the perturbing mirror may have a concave curvature.

A beam may be injected into and exit from the improved multi-pass cell in a variety of different ways. In one implementation, the beam may be injected through and exit from an off-axis coupling hole formed in the front mirror or the back mirror. Alternatively, the beam may be injected via, and exit via, a diverter mirror located proximate to the center of the front mirror or the back mirror. In still another alternative, the beam may be injected via, and exit via, a diverter mirror located proximate to an outer edge of the front mirror or the back mirror. A variety of other alternatives are also possible.

In one embodiment, the improved multi-pass cell may be constructed according to a setup procedure. As part of the procedure, a base pattern is selected and a base pattern shape is set. Further, a pattern multiplication factor is selected. Then the perturbing mirror spacing and a radius of curvature may be selected. In one technique, the perturbing mirror spacing may be calculated based, at least in part, on the spacing between the front mirror and the back mirror and the pattern multiplication factor. Further, the radius of curvature of the perturbing mirror may be calculated based, at least in part, on the perturbing mirror spacing, the pattern multiplication factor, and a radius of curvature of the front mirror and the back mirror. A multi-pass cell is then assembled with a perturbing mirror having the radius of curvature placed at the perturbing mirror spacing from the back mirror, wherein the radius of curvature of the perturbing mirror and the perturbing mirror spacing cause the perturbing mirror to circulate the pattern having the pattern shape according to the multiplication factor.

The improved multi-pass cell may offer a variety of advantages. For example, as a result of the design, the front mirror, the back mirror and the perturbing mirror may each be constructed as spherical mirrors, which are economical to produce. Further, high optical throughput may be provided, utilizing an overall pattern that is well matched to round mirrors, so that the cell's volume is well filled. Further, the number of passes may be readily adjusted by changing the pattern multiplication factor via axial translation of the perturbing mirror to a different perturbing mirror spacing. Alternatively, different pattern multiplication factors may be achieved by moving the perturbing mirror and the back mirror axially as a unit, while maintaining a fixed perturbing mirror spacing.

It should be understood that the example embodiments discussed in this Summary may include a variety of other features, including other features discussed below, and variations thereof. Further a variety of other example embodiments may be utilized. This Summary is intended simply as a brief introduction to the reader, and does not imply that the specific features mentioned herein are all the features of the invention, or are essential features of the invention.

BRIEF DESCRIPTION OF THE DRAWINGS

The text refers to the accompanying drawings, of which.

DESCRIPTION

Physical Arrangement and Operation

Figure 1:
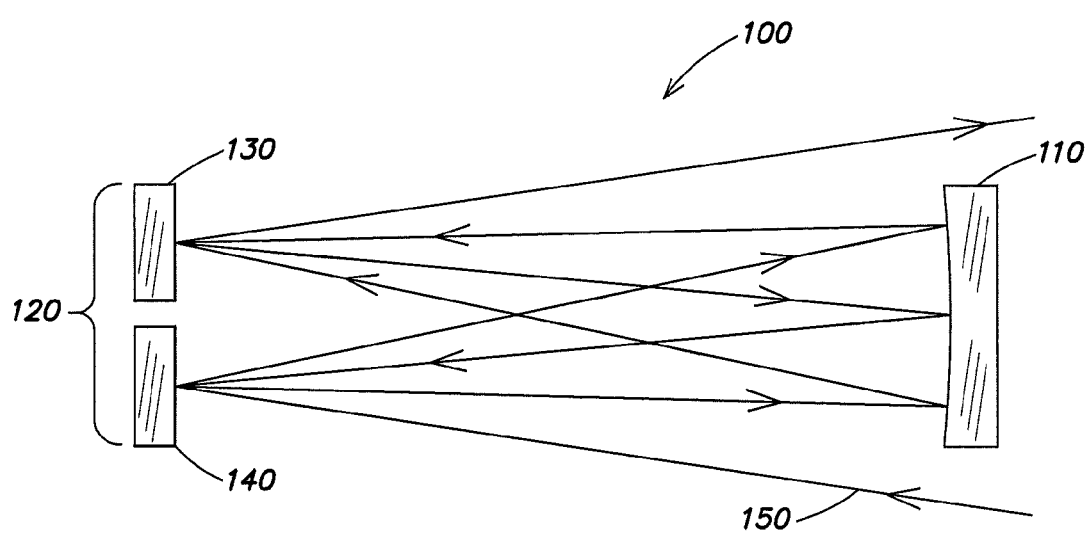
FIG. 1 is diagram depicting an example White cell.
Figure 2:
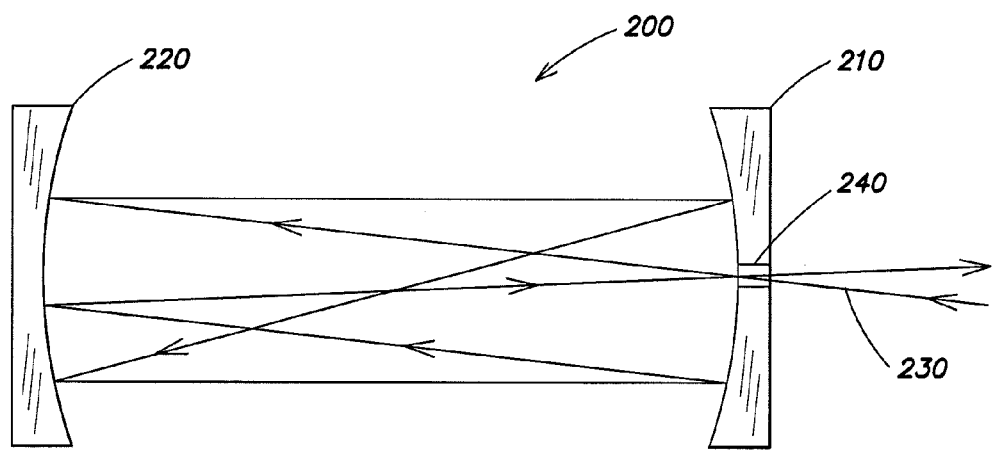
FIG. 2 is a diagram depicting an example Herriott cell.
Figure 3:
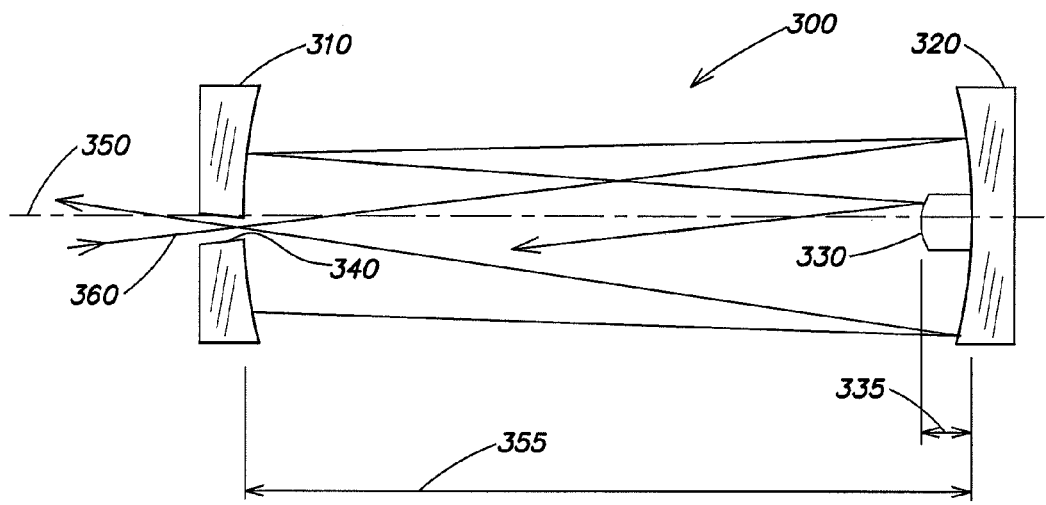
FIG. 3 is a diagram depicting an example improved multi-pass cell having an off-axis coupling hole formed in a concave front mirror, and a convex perturbing mirror located a perturbing mirror spacing in front of the concave back mirror.

FIG. 3 is a diagram depicting an example improved multi-pass cell 300 having an off-axis coupling hole 340 formed in a concave front mirror 310, and a convex perturbing mirror 330 located at a perturbing mirror spacing 335 in front of the concave back mirror 320. The perturbing mirror spacing 335 may be significantly less than a spacing 355 between the front mirror and the back mirror, such that the perturbing mirror 330 is disposed close to the back mirror 320.

It should be understood that in alternative implementations, the off-axis coupling hole 340 may be formed in the back mirror 320. Further, it should be understood that in alternative implementations the perturbing mirror may located at a perturbing mirror spacing 335 behind the back mirror 320 and have a concave shape. In such an alternative implementation, the back mirror 320 may have a hole formed therein to expose the perturbing mirror. The front mirror 310, the back mirror 320, and the perturbing mirror 330 are each centered upon an axis 350 of the multi-pass cell 300. In the shown example, the front mirror 310 and back mirror may each share the same first diameter, with the perturbing mirror having a second, smaller diameter. However, in alternative implementations, the front and back mirrors may have unequal diameters. The front mirror 310, the back mirror 320, and the perturbing mirror 330 may each be constructed as spherical mirrors, that are generally inexpensive to produce. However, in alternative implementations, they may be constructed to have different types of surfaces.

A beam 360 from a light source (e.g., a laser) (not shown) may be injected into the improved multi-pass cell 300 via an off-axis coupling hole 340 formed in the front mirror 310. The beam 360 may be reflected according to a base pattern (e.g., a generally elliptical Herriott cell pattern) that provides a particular number of passes. At the completion of the base pattern, the beam may impact the perturbing mirror 330 which introduces a rotation about the axis 350 of the cell 300 at an angle. The base pattern may then be repeated in a rotated iteration. Successive base patterns and rotations thereof may be performed to circulated base pattern about the cell, effectively multiplying the number of passes of the base pattern by a pattern multiplication factor equal to the number of rotations. While FIG. 3 shows a few example passes, practical implementations may provided hundreds of passes. The overall pattern may well match the shape of a round front mirror 310 and back mirror 320. While the base pattern may have a shape other than round (e.g., a generally elliptical shape), the successive rotations may produce an overall pattern of generally round shape that is well matched to round front mirrors and back mirrors, so that the cell's volume is well filled. Upon completion of the overall pattern, the beam 360 may exit the cell 300 via the off-axis coupling hole 340.

To change the pattern multiplication factor, and thereby adjust the number of passes achieved before the beam 360 exists the cell 300, the perturbing mirror spacing 335 may be adjusted. When the perturbing mirror 330 is translated along axis 350 to bring the perturbing mirror 330 nearly flush with the back mirror 320, the pattern multiplication factor may be reduced to 1, and the overall pattern may approximate the base pattern (e.g., a Herriott cell pattern). At a substantial perturbing mirror spacing, a substantial pattern multiplication factor (e.g., 16× or greater) may be achieved. Alternatively, the pattern multiplication factor may be changed by moving the perturbing mirror 330 and the back mirror 330 along axis 350 as a unit, thereby changing the spacing between the front mirror and the back mirror 355, while maintaining a fixed perturbing mirror spacing 335.

Figure 4:
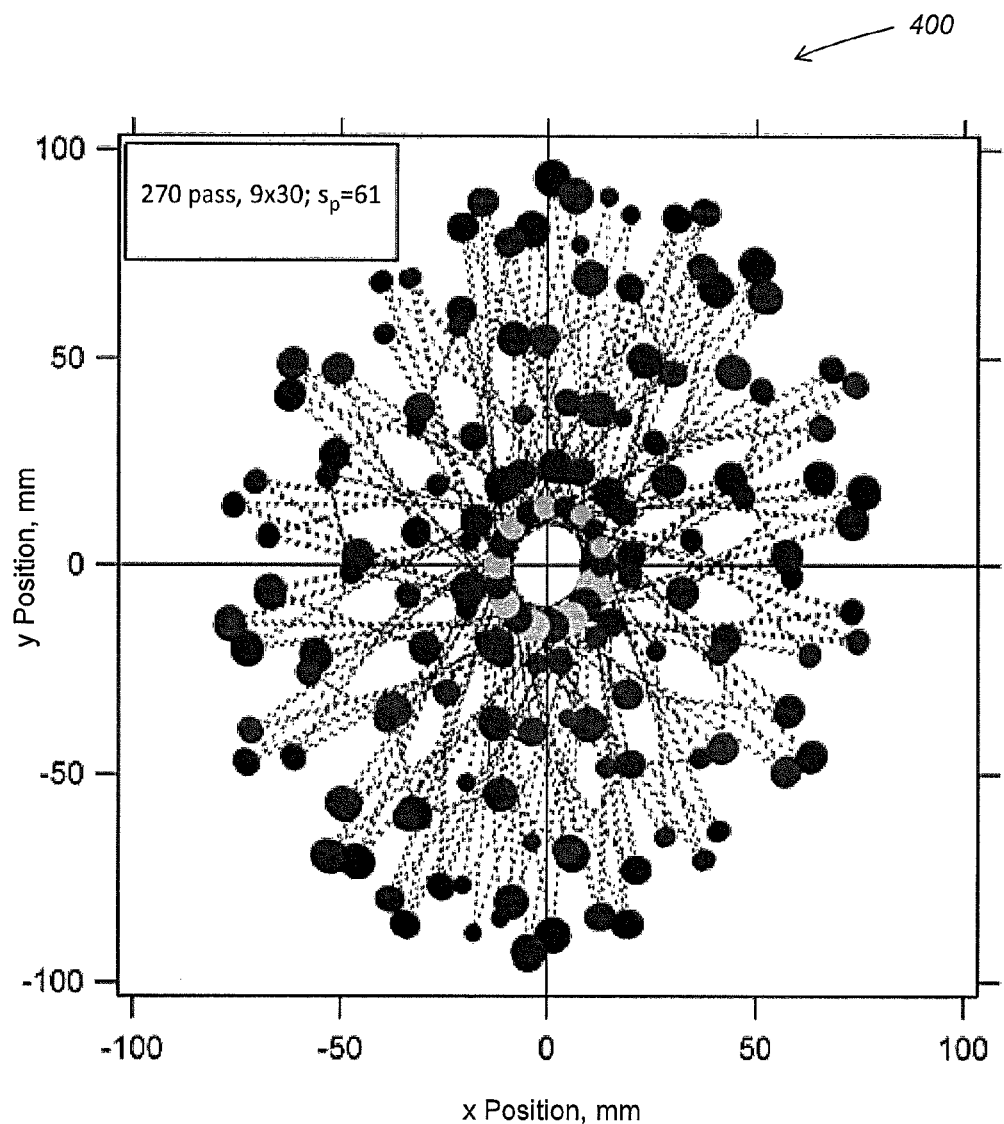
FIG. 4 is an illustration of an example pattern that may be produced by the improved multi-pass cell of FIG. 3.

FIG. 4 is an illustration of an example pattern 400 that may be produced by the improved multi-pass cell of FIG. 3. In this example, the base pattern is a 30 pass Herriott cell pattern producing a generally elliptical arrangement of spots, and the pattern multiplication factor is 9, such that the pattern 400 provides 270 passes. Such an arrangement may offers 150 meters of path length in a cell having 1 liter of volume. The illustration depicts spots on all mirror surfaces (e.g., the front mirror, the back mirror, and the perturbing mirror). The spot diameters decrease as the pass number increases. In general, a small output spot size may be achieved.

Figure 5:
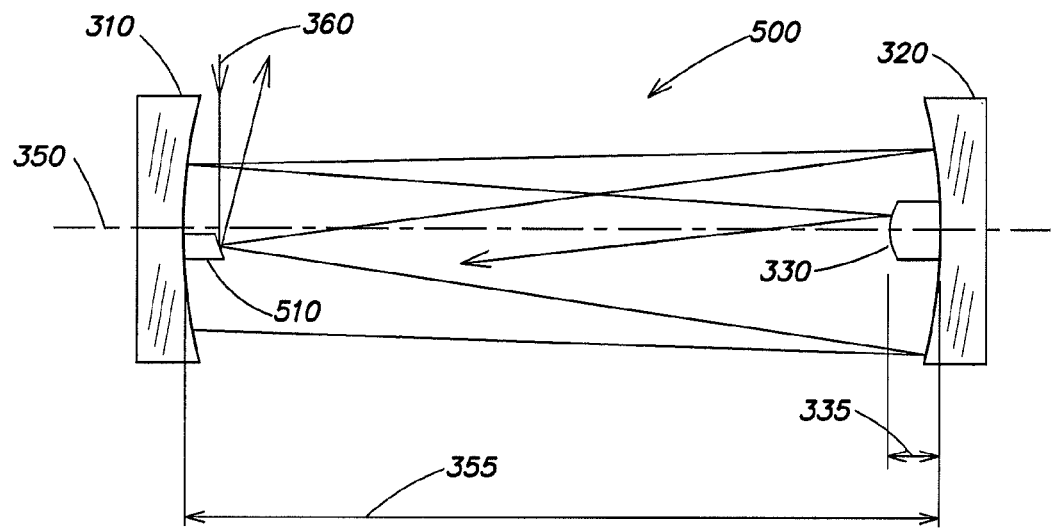
FIG. 5 is a diagram depicting an improved multi-pass cell having a diverter mirror located proximate to the center of the front mirror.

FIG. 5 is a diagram depicting an improved multi-pass cell 500 having a diverter mirror 510 located proximate to the center of the front mirror 310. It should be understood that in alternative implementations, the diverter mirror 510 may be located on the back mirror 320 proximate to its center, for example, just beyond the extent of the perturbing mirror 330. A location may be considered proximate to the center of a mirror if it is within the inner 25% of the radius of the mirror.

The cell 500 of FIG. 5 may operate similar to the cell 300 discussed above, however the beam 360 may be injected via, and exit via, the diverter mirror 510 rather than passing through a coupling hole. In some cases, the beam 360 may be injected into the multi-pass cell substantially perpendicular to the axis 350, and the diverter mirror 510 may redirect the beam to begin the first base pattern. Similarly, the diverter mirror 510 may pass the beam 360 upon completion of the final base pattern out of the cell substantially perpendicular to the axis 350. In such manner, there may be no need to drill a coupling hole in front mirror 310 or the back mirror 320 to permit passage of the beam 360.

Figure 6:
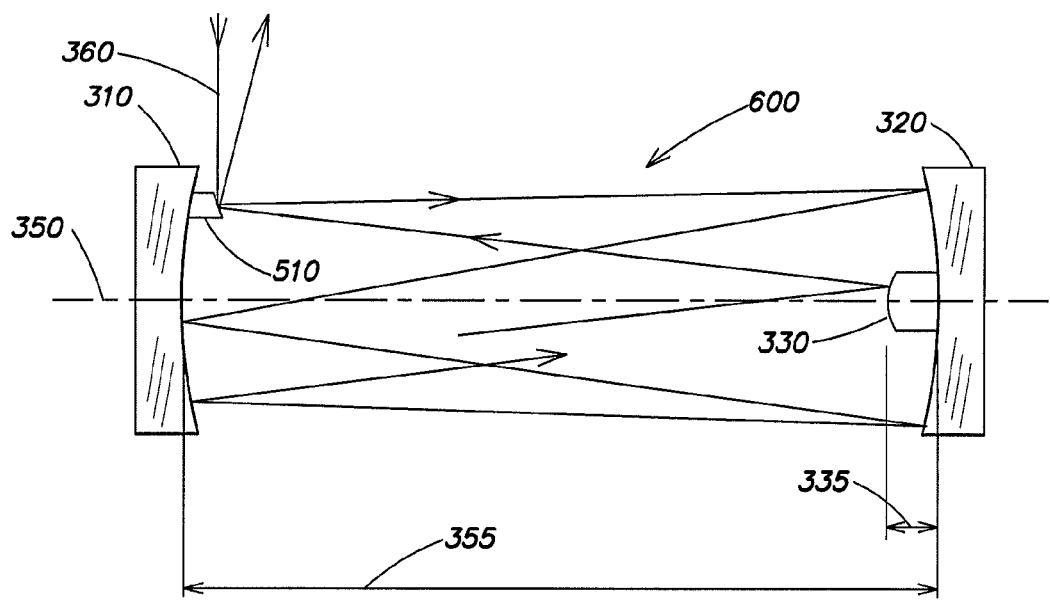
FIG. 6 is a diagram depicting an improved multi-pass cell having a diverter mirror located proximate to an outer edge of the front mirror.

FIG. 6 is a diagram depicting an improved multi-pass cell 600 having a diverter mirror 510 located proximate to an outer edge of the front mirror 310. It should be understood that in alternative implementations, the diverter mirror 510 may be located on the back mirror 320 about its outer edge. A location may be considered proximate to the outer edge of a mirror if it is within an outer 25% of the radius of the mirror. This alternative design may operate similarly to the design shown in FIG. 5.

Paraxial Theory

The operation of the improved multi-pass cell may be understood by reference to paraxial theory. The theory may be presented as paraxial matrices, which yield circulation angles and conditions for stability for the improved multi-pass cell.

Considering first a multi-pass cell (a "base cell") that has been adjusted so that a re-entrant condition is established (i.e. a beam injected into the cell returns to its initial state after $N_{Po}$ passes). In terms of paraxial matrix theory, the cell matrix is identity for the re-entrant condition. If the matrix representing one pass through the cell is C, and the matrix for N traversals is represented as $C^N$, then for $N=N_{Po}$, $C^N=I$. A perturbing mirror may then be introduced half way through the base multi-pass cell's propagation, changing the optical path. The perturbing mirror may influence two passes of the cell, with one radius change and two space changes. The perturbed traversal, after N passes, is described by:

$$M = [C^{N/2-1} P\ C^{N/2-1}],$$

where matrix P represents the two perturbed passes. The base cell is configured so that the beam is at the back mirror after $N_{po}/2$ passes, which requires that $N_{po}/2$ be odd. With the base pattern, $C^{N/2}=\pm I$, and the perturbed matrix, after $N_{po}$ passes is given by the form, $[C^{-1}\ P\ C^{-1}]$.

The matrix for the perturbed matrix after $N_{po}$ passes, $[C^{-1} P\ C^{-1}]$, can be viewed as a super-cycle cell, which itself may be closed after $N_x$ repetitions. In order for the initial beam to return to its original state, $N_{Po}*N_x$ passes are required. Expressions for $[C^{-1}\ P\ C^{-1}]^{Nx}$ can be used to derive an advance angle, stability and closure conditions for the super-cycle.

A paraxial ABCD matrix basis may be used. For simplicity, one transverse dimension description may be used where possible. In one case the state vector ($\mathbf{Y}$) is:

$$\mathbf{Y} = \begin{vmatrix} y \\ \hat{y} \end{vmatrix},$$

where y is position and $\hat{y}$ is slope. Optical elements may be represented by 2×2 matrices which modify the state vector. Sequential multiplication by optical element matrices may represent the effect of an optical system on the initial beam state. In one example, the relevant optical elements may be:

a space, $$S = \begin{vmatrix} 1 & s \\ 0 & 1 \end{vmatrix}$$

and a reflection, $$R = \begin{vmatrix} 1 & 0 \\ -g & 1 \end{vmatrix}, g = 2/r_c,$$

where s is the mirror spacing and $r_c$ is the mirror radius of curvature. One traversal of a cell may be represented by reflection then propagation:

$$C = SR = \begin{vmatrix} (1-gs) & s \\ -g & 1 \end{vmatrix}, \text{ or with } (1-gs) = \alpha, \begin{vmatrix} \alpha & s \\ -g & 1 \end{vmatrix}.$$

For a system (M) with N traversals, $M=C^N$. A closed expression for $M=C^N$ may be available from Sylvester's theorem, as:

$$M^N = \begin{vmatrix} A & B \\ C & D \end{vmatrix}^N =$$

-continued $$(\sin\theta)^{-1}\begin{vmatrix} (A\sin(N\theta) - \sin((N-1)\theta)) & (B\sin(N\theta)) \\ (C\sin(N\theta)) & (D\sin(N\theta) - \sin((N-1)\theta)) \end{vmatrix},$$

where $\cos\theta = (A+D)/2$. For example, $\cos\theta = (2-gs)/2 = 1-s/r$. If $N\theta = m\,2\pi$, for integer m, then $M^N = I$, and the system matrix reproduces the initial beam state.

Suppose that a cell which is adjusted to the re-entrant condition has a perturbing mirror half way through the propagation, $S' = S(s')$, $R' = R(g_p)$. The perturbing mirror influences two passes of the cell, with one radius change and two space changes, so that:

$$M' = C \ldots C[S'R'S'R_o]C \ldots C = C^{N/2-1}[S'R'S'R_o]C^{N/2-1}.$$

Using that $C^{N/2-1} = C^{N/2}\,C^{-1}$, then $M' = C^{N/2}\,C^{-1}\,[S'R'S'R_o]\,C^{-1}\,C^{N/2}$. With the re-entrant condition, $C^{N/2} = \pm I$, the two $C^{N/2}$ multiplications are equivalent to unity. That is:

$$M' = C^{-1}[S'R'S'R_o]C^{-1}.$$

Use that: $C^{-1} = [S\,R]^{-1} = R^{-1}\,S^{-1} = R(-g_o)\,S(-s_o)$, and $s' = s_o - S_p$.

$$M' = R(-g_o)S(-s_o)S(s_o - s_p)R(g_p)S(s_o - s_p)R(g_o)R(-g_o)S(-s_o),$$

$$= R(-g_o)S(-s_o)S(s_o)S(-s_p)R(g_p)S(-s_p)S(s_o)R(g_o)R(-g_o)S(-s_o),$$

$$= R(-g_o)S(-s_p)R(g_p)S(-s_p)S(s_o)S(-s_o),$$

$$M' = R(-g_o)S(-s_p)R(g_p)S(-s_p),$$

$$M' = \begin{vmatrix} 1 & 0 \\ +g_o & 1 \end{vmatrix}\begin{vmatrix} 1 & -s_p \\ 0 & 1 \end{vmatrix}\begin{vmatrix} 1 & 0 \\ -g_p & 1 \end{vmatrix}\begin{vmatrix} 1 & -s_p \\ 0 & 1 \end{vmatrix},$$

$$= \begin{matrix} (1+s_pg_p) & (-s_p(2+s_pg_p)) \\ (+g_o - g_p(1-s_pg_0)) & (-s_pg_0 + (1-s_pg_0)(1+s_pg_0)) \end{matrix}.$$

Call: $\alpha_{pp} = (1+s_pg_p)$, $\alpha_{po} = (1-s_pg_o)$, then, $$M' = \begin{vmatrix} \alpha_{pp} & (-s_p(1+\alpha_{pp})) \\ (+g_o - g_p\alpha_{po}) & (-s_pg_o + \alpha_{po}\alpha_{pp}) \end{vmatrix}.$$

For the "round trip" matrix M', the advance angle is given by:

$$\cos\theta' = [\alpha_{pp} - s_pg_o + \alpha_{po}\alpha_{pp}]/2 = [\alpha_{pp} + \alpha_{po} - 1 + \alpha_{po}\alpha_{pp}]/2.$$

Defining that $\gamma_{pp} = (\alpha_{pp}+1)/2$ and $\gamma_{po} = (\alpha_{po}+1)/2$ [$\gamma_{pp} = 1+s_p/r_p$, $\gamma_{pO} = 1-s_p/r_o$], then $\cos\theta' = 2\gamma_{pp}\,\gamma_{pp} - 1$. For system stability the condition that $-1 < \cos\theta'1$, should be satisfied so that $0 < \gamma_{pp}\,\gamma_{po} < 1$. The range of such system stability may be shown by a stability diagram.

Figure 7:
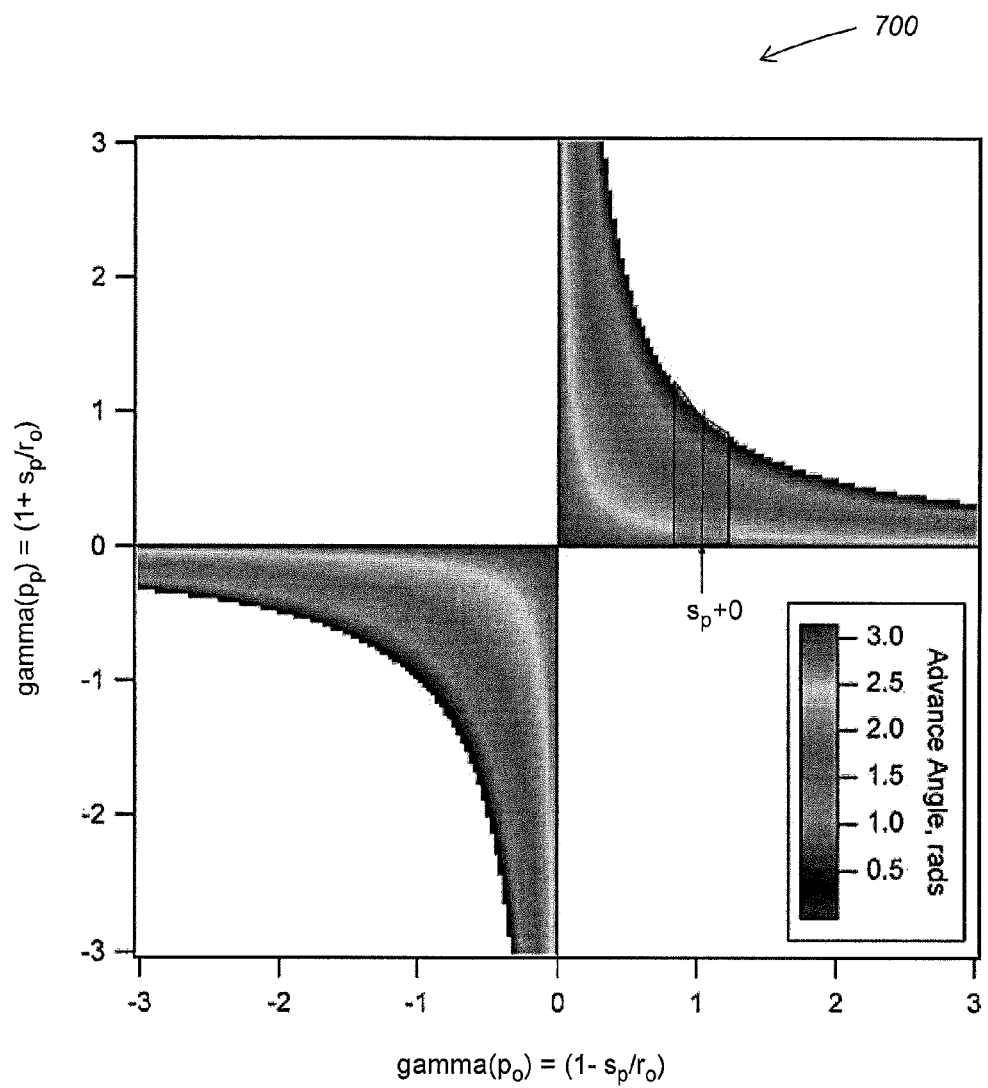
FIG. 7 is a stability diagram showing stability of one particular design for an improved multi-pass cell.

FIG. 7 is a stability diagram 700 showing stability of one particular design for an improved multi-pass cell. While mathematical conditions may be satisfied anywhere in the shaded area, physical considerations may further reduce the available useful area. For example, consider a system where the perturbing mirror spacing, $s_p$, is small compared to the spacing between the front and back mirror, and hence is small compared to the radius, $r_o$, of the front and back mirror. That confines the system to a zone 710 in the right branch near $s_p = 0$. In most of the useful zone, $\gamma_{pp} < 1$, which makes $s_p/r_p < 0$. One may have two types of setup conditions for the improved multi-pass cell: a) $s_p > 0$ indicating the perturbing mirror is located forward of the back mirror, and $r_p < 0$ indicating it has a convex curvature; and b) $s_p < 0$ indicating the perturbing mirror is located behind the back mirror, and $r_p > 0$ indicating it has a concave curvature.

Geometry of Optical Paths and Setup Procedure

Figure 8:
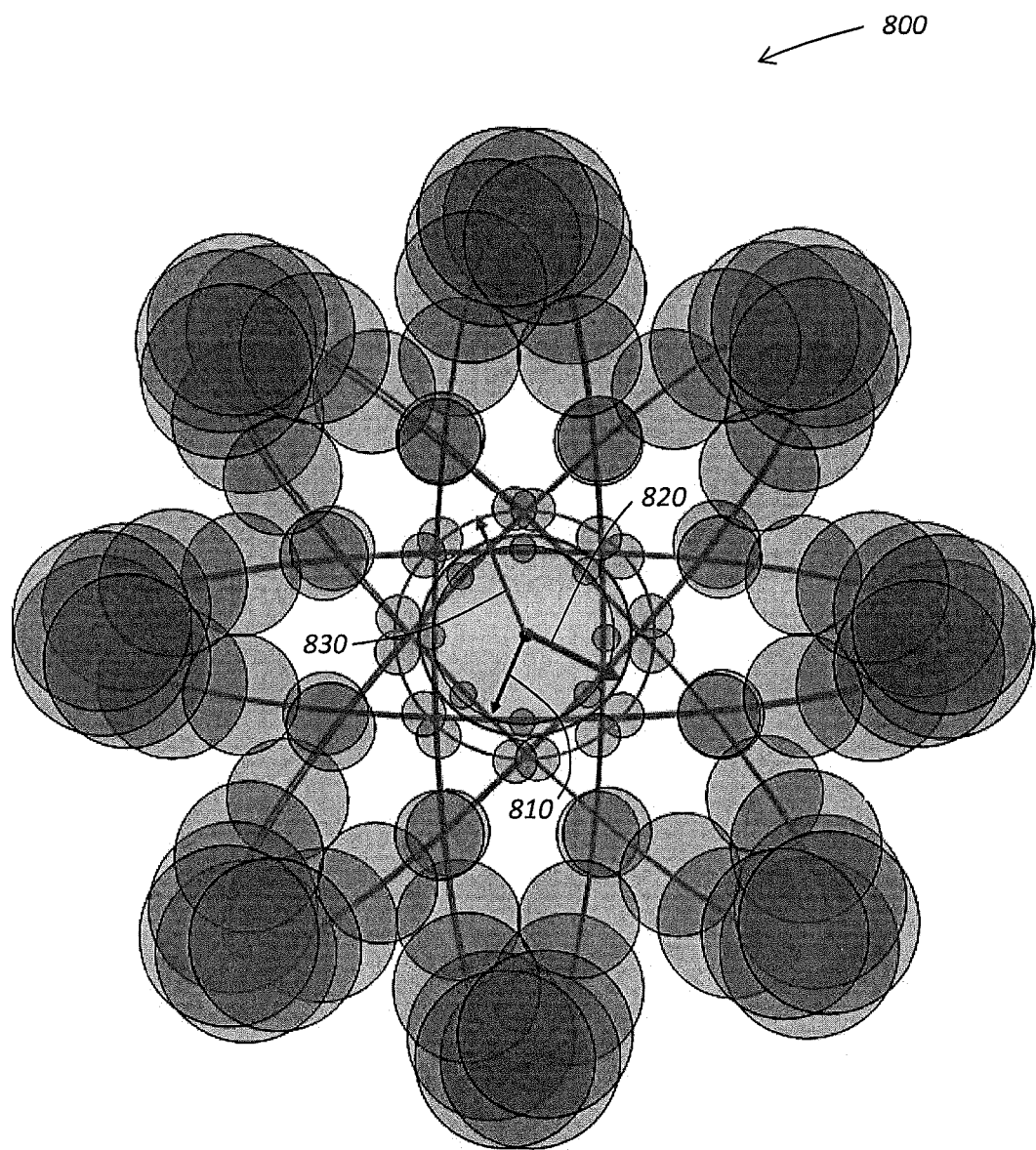
FIG. 8 is an illustration of an example pattern showing example rings of spots and relevant radii.

As discussed above, the improved multi-pass cell may replicate and rotate a base pattern of reflections (e.g., a Herriott cell pattern). A set of rings of spots are thus generated. FIG. 8 is an illustration of an example pattern 800 showing the example rings of spots and relevant radii. The innermost ring at radius $\rho_{so} = X_o$ 810 is defined by the location of the coupling hole or diverter mirror. The second ring is defined by the pair of points opposite the coupling hole or diverter mirror, above and below the x-axis. The radius of the second ring of points ($\rho_{si}$) 820 should be sufficiently large that these spots lie outside the first ring. The radius of the perturbing mirror ($r_{pm}$) 830 may be between the first and second ring of spots.

Figure 9:
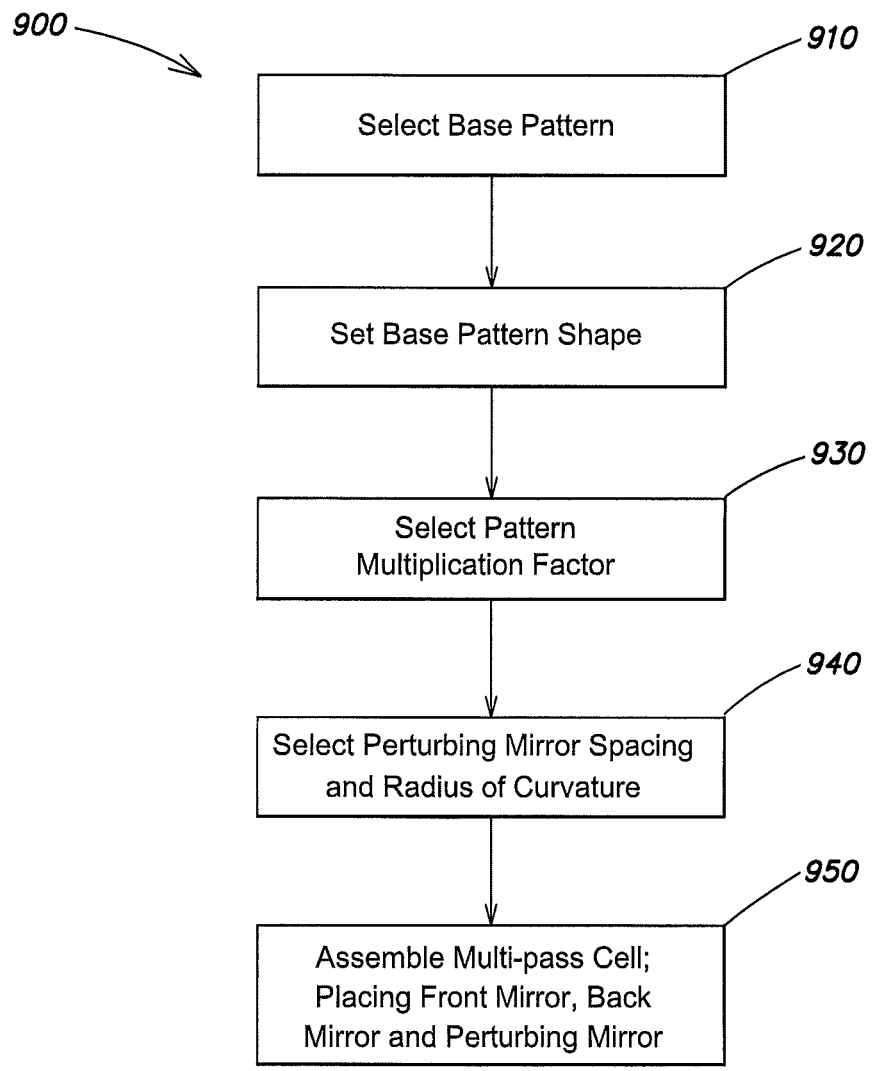
FIG. 9 is a flow diagram of an example sequence of steps to setup an improved multi-pass cell.

An improved multi-pass cell with this geometry may be constructed according to a setup procedure. FIG. 9 is a flow diagram of an example sequence of steps 900 to setup an improved multi-pass cell. While certain aspects of this example are specific to a cell including an offset coupling hole and a convex perturbing mirror located in front of the back mirror, it should be understood that the steps may be readily adapted for use with other implementations. At step 910, base pattern is selected. The base pattern may be selected based on the front and back mirror's radius of curvature, $R_{co}$, and spacing, $S_o$, such that $s_o = r_{co}(1-\cos(\theta_R))$. A recirculation pattern may be used where there is a return to the (±) coordinates of the origin after $N_{po}/2$ passes, but at the back mirror, i.e. $C^{N/2} = \pm I$ with odd $N_{po}/2$. For reproducing the origin coordinates at the back mirror, $(N_{po}/2)\,\theta_R = \pi M$, for integer M. If M is even then $C^{N/2} = +I$, and the spot at $N_{po}/2$ passes is at the (x, y) coordinates of the origin, and the front and back mirror spot patterns overlap (in projection to a single x, y plane). If M is odd then $C^{N/2} = -I$, and the spot at $N_{po}/2$ passes is at the (-x, -y) coordinates of the origin, and the front and back mirror spot patterns do not overlap (in projection to a single x, y plane). Often, one can expect the number of passes of the base pattern to be approximately 20 to 40. The pattern parameters, $\{N_{po}, M\}$, may be further selected in terms of wide numerical separation of subsequent beam spots, in order to minimize interference fringes.

At step 920, a base pattern shape is set. Two points may determine the unperturbed pattern shape, the origin $(x_o, y_o)$ and the aim-in point $(x_1, y_1)$. If $y_o = 0$, the unperturbed ellipse of beam points is given by:

$$x_j = s_x \sin(j\,\theta_R) + c_x \cos(j\,\theta_R);\; y_j = s_y \sin(j\,\theta_R),$$

where:

$s_x = [x_1 - x_0 \cos(\theta_R)]/\sin(\theta_R)$;
$c_x = x_0$;
$s_y = y_1/\cos(\theta_R)$.

The pattern vertical size ($s_y$) may be set by $y_1$ and the horizontal size ($c_x$) by $x_0$. The vertical size may be set so that the largest spot ($r_{so}$) at the outside of the pattern still fits on the mirror ($r_{mo}$): $s_y = (r_m - r_{so})$. Above and below $y=0$, the closest spots in y will be at $y_{si} \approx \pm 2\pi\,s_y/N_p$. In the overall pattern, there will be an innermost ring of spots at radius $x_0$. There will be a second ring of spots at radius $\rho_{si} = (x_o^2 + y_{si}^2)^{1/2}$. The pattern vertical size, number of passes and horizontal size may be chosen so that the second ring of spots is sufficiently greater in radius than the first ring. The radius of the perturbing mirror may then be between $x_0$ and $\rho_{si}$.

At step 930, a pattern multiplication factor is selected. For a given pattern multiplication factor $N_x$, there will be $N_x$ spots in the inner ring on the front mirror, and on the perturbing mirror. Those spots should be widely spaced enough for clean coupling in and out at the front mirror. With a coupling hole radius $r_h$, $N_x$ hole diameters fit in a ring: $N_x = \pi\,x_o/r_h$. As such, $N_x$ should to be consistent with the coupling hole size.

Figure 10:
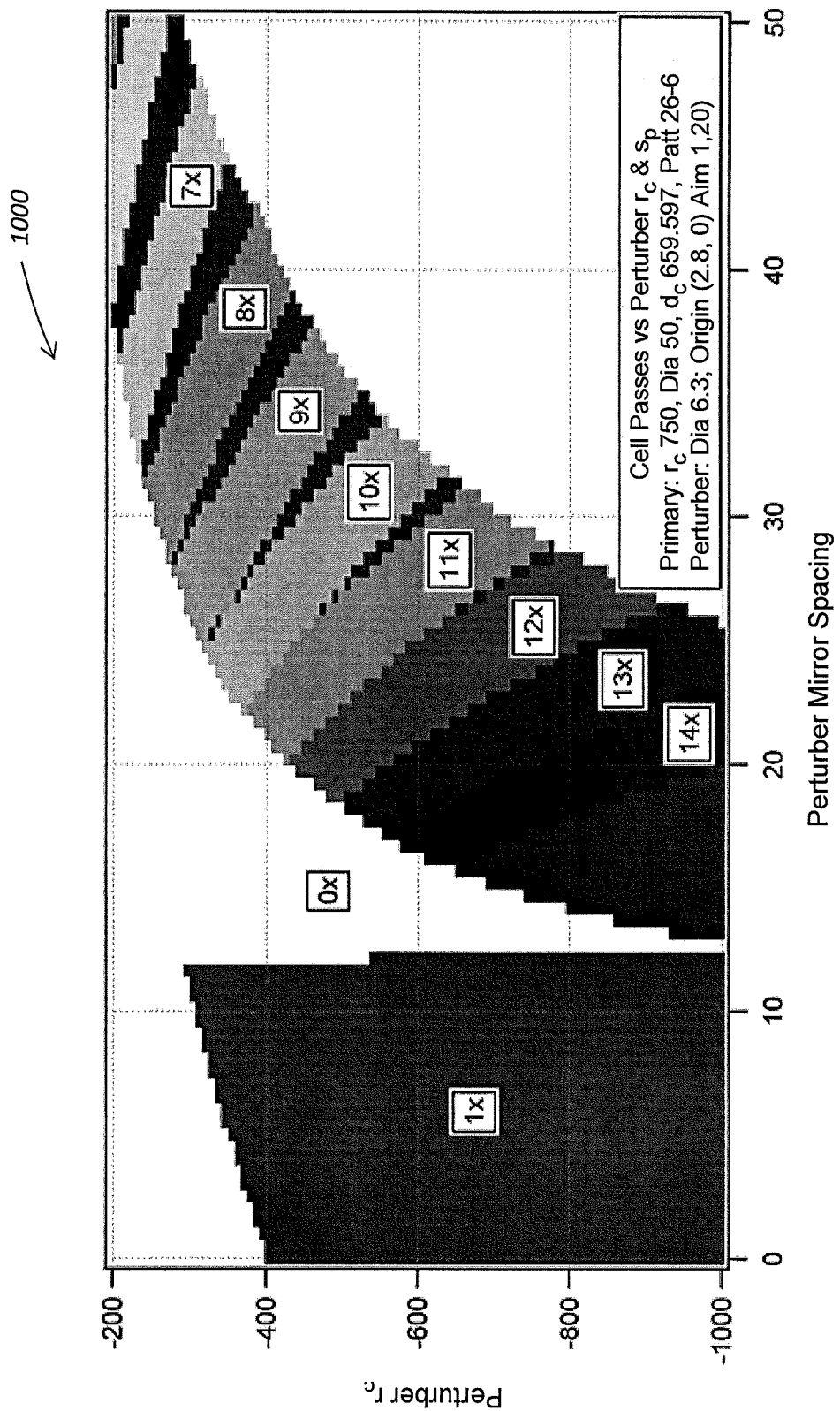
FIG. 10 is an example map that may be produced from results of a ray-tracing program for a particular base pattern.

At step 940, the perturbing mirror spacing and a radius of curvature for the perturbing mirror may be selected. In one technique, system parameters may be systematically varied, and a ray tracing program used to produce maps of all possible values. The maps may change with changes in the base-pattern of the cell, and be specific to the particular choices of $\{x_0, x_1, y_1\}$. Using the maps, useful perturbing mirror spacing and radius of curvature may be determined. FIG. 10 is an example map 1000 that may be produced from results of a ray-tracing program for a particular base pattern. Shaded areas are labeled with the produced pattern multiplication factor. White areas are where the beam fails to exit the cell.

In another technique, perturbing mirror spacing may be calculated based, at least in part, on a distance between the front mirror and the back mirror and the pattern multiplication factor. Further, the radius of curvature of the perturbing mirror may be calculated based, at least in part, on the perturbing mirror spacing, the pattern multiplication factor, and a radius of curvature of the front mirror and the back mirror. For example, the perturbing mirror spacing may be calculated by the formula:

$$s_p = (d_c x_o / y_1) \sin(\pi/N_x),$$

where $x_o$ is the origin of the x-axis, $y_1$ is a y-axis coordinate of the aim-in point for the beam, $d_c$ is a distance between the front mirror and the back mirror, and $N_x$ is the pattern multiplication factor. With perturbing mirror spacing determined, the stability equation discussed above may be used to determine the perturbing mirror's radius of curvature, $r_{cp}$, by:

$$r_{cp} = s_p / [-1 + (1 + \cos(2\pi/N_x))/2(1 - s_p/r_{co})],$$

where $r_{co}$ is the primary mirror radius of curvature.

At step 950, an improved multi-pass cell is assembled by placing the front mirror, placing the back mirror, and placing the perturbing mirror having the radius of curvature at the perturbing mirror spacing from the back mirror, wherein the radius of curvature of the perturbing mirror and the perturbing mirror spacing cause the perturbing mirror to circulate the pattern having the pattern shape according to the multiplication factor.

Figure 11:
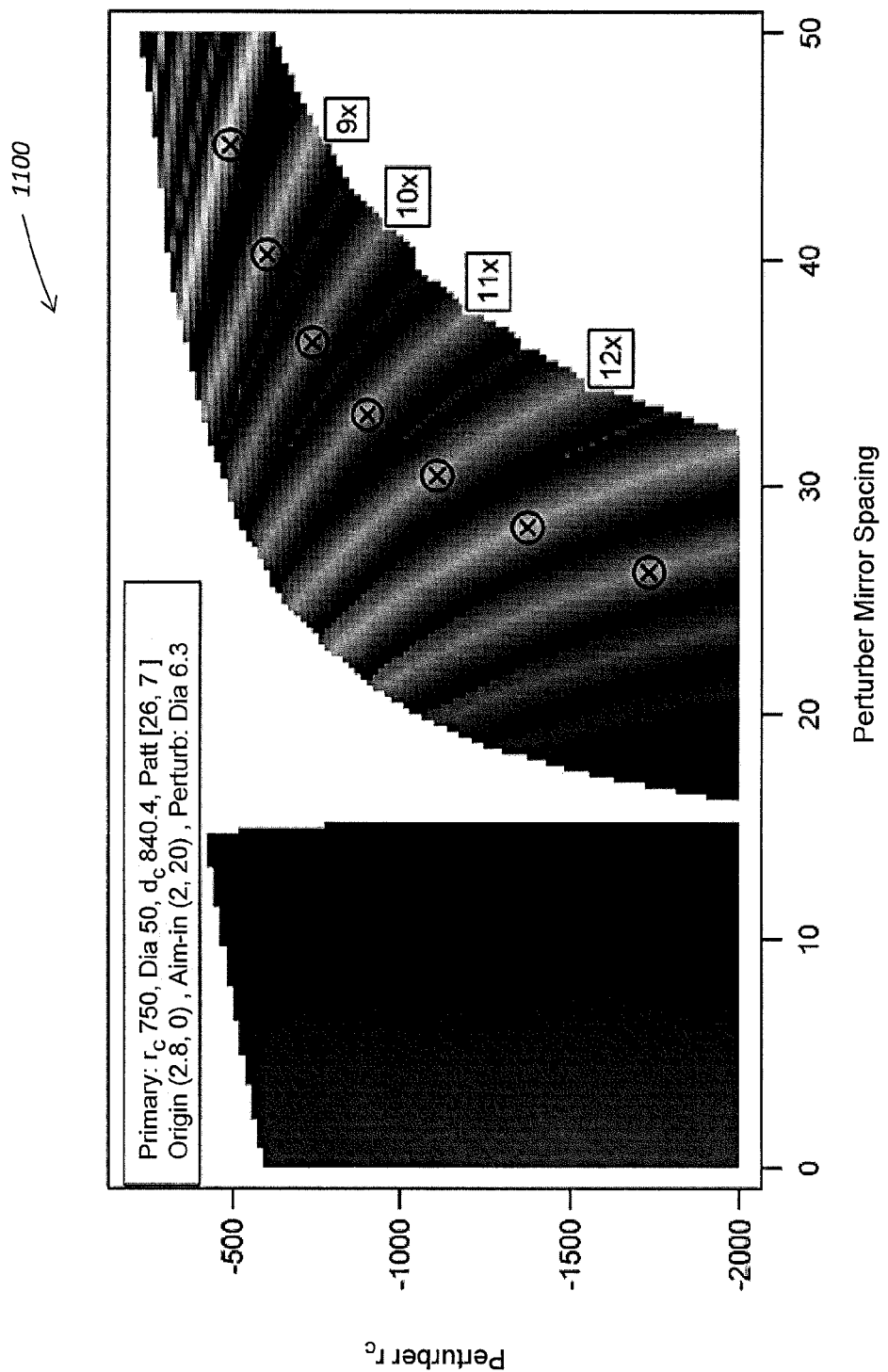
FIG. 11 is an example map that includes various calculated perturbing mirror spacing and radii of curvature superimposed.

FIG. 11 is an example map 1100 that includes calculated perturbing mirror spacing and radius of curvature of the perturbing mirror superimposed. In this map, the shading represents the position error of the returning beam spot. The darker shading indicates more error. The superimposed points from the formulas are regions of relatively low error.

In summary, the example embodiments discussed above set forth an improved multi-pass cell for a long path-length spectrometer that includes a perturbing mirror that causes a base pattern of reflections (e.g., a Herriott cell pattern) to be repeated multiple times, where each subsequent base pattern is rotated about an axis of the cell at an angle from a prior base pattern. It should be understood that various components of the improved multi-pass cell may be modified, added to, removed, or otherwise changed depending on the implementation. In addition, it should be understood that various selections and calculations discussed above may be performed using a variety of different types of hardware, software, and combination thereof. The hardware may include a variety of types of computing systems having processors, memory chips, programmable logic circuits, application specific integrated circuits, and/or other types of components that support execution of software. The software may include executable instructions that implement applications stored in non-transitory electronic device-readable media, such as a volatile or persistent memory devices, hard-disks, or other data stores. Combinations of hardware and software may be adapted to suit different environments and applications. In general, it should be understood that the above descriptions are meant to be taken only by way of example.

What is claimed is:

1. A multi-pass cell for a spectrometer, comprising:
   a concave front mirror centered along an axis of the multi-pass cell;
   a concave back mirror centered along the axis and facing the front mirror; and
   a perturbing mirror centered along the axis, facing the front mirror, and offset from the back mirror by a perturbing mirror spacing, the perturbing mirror either having either a convex curvature and being offset in front of the back mirror relative to the front mirror or having a concave curvature and being offset behind the back mirror relative to the front mirror,
   wherein the perturbing mirror is configured to cause a base pattern of reflections of a beam injected into the multi-pass cell to be repeated multiple times, each subsequent base pattern rotated about the axis at an angle from a prior base pattern.

2. The multi-pass cell of claim 1, wherein the base pattern is a Herriott cell pattern.

3. The multi-pass cell of claim 1, wherein the front mirror, the back mirror and the perturbing mirror are each spherical mirrors.

4. The multi-pass cell of claim 1, wherein the perturbing mirror has a convex curvature and is disposed in front of the back mirror relative to the front mirror.

5. The multi-pass cell of claim 1, wherein the perturbing mirror has a concave curvature and is disposed behind the back mirror relative to the front mirror.

6. The multi-pass cell of claim 1, wherein the front mirror includes an off-axis coupling hole through which the beam is injected into the multi-pass cell and via which the beam exits the multi-pass cell.

7. The multi-pass cell of claim 1, further comprising a diverter mirror coupled to the front mirror or the back mirror, and configured to receive and redirect the beam as the beam is injected into the multi-pass cell.

8. The multi-pass cell of claim 7, wherein the diverter mirror is coupled to the front mirror.

9. The multi-pass cell of claim 7, wherein the diverter mirror is coupled to the back mirror.

10. The multi-pass cell of claim 7, wherein the diverter beam is located proximate to the center of the front mirror or the back mirror.

11. The multi-pass cell of claim 7, wherein the diverter beam is located proximate to an outer edge of the front mirror or the back mirror.

12. The pass cell of claim 1, wherein the perturbing mirror spacing ($s_p$) is set as:

$$s_p = (d_c x_o / y_1) \sin(\pi/N_x),$$

where $x_o$ is the origin of an x-axis of a coordinate system, $y_1$ is a y-axis coordinate of an aim-in point for the beam, $d_c$ is a distance between the front mirror and the back mirror, and $N_x$ is a multiplication factor.

13. The multi-pass cell of claim 1, wherein a radius of curvature of the perturbing mirror ($r_{cp}$) is set as:

$$r_{cp} = s_p / [-1 + (1 + \cos(2\pi/N_x))/2(1 - s_p/r_{co})],$$

where $s_p$ is the perturbing mirror spacing, $N_x$ is the pattern multiplication factor and $r_{co}$ is a radius of curvature of the front mirror and the back mirror.

14. A multi-pass cell for a spectrometer, comprising:
a concave front mirror;
a concave back mirror facing the front mirror; and
a convex perturbing mirror facing the front mirror, the perturbing mirror offset in front of the back mirror back mirror relative to the front mirror by a perturbing mirror spacing,
wherein the perturbing mirror is configured to cause a base pattern of reflections of a beam injected into the multi-pass cell to be repeated multiple times, each subsequent base pattern rotated from a prior base pattern.

15. The multi-pass cell of claim 1, wherein the base pattern is a Herriott cell pattern.

16. A method for constructing a multi-pass cell for a spectrometer, comprising:
selecting a base pattern of reflections for a beam injected into the multi-pass cell, the selected base pattern including a plurality of reflections between a front mirror and a back mirror of the multi-pass cell;
setting an a base pattern shape, the pattern shape defining a horizontal and a vertical size of the base pattern;
calculating a pattern multiplication factor that indicates how many time the base pattern will circulate;
calculating a perturbing mirror spacing and a radius of curvature for a perturbing mirror;
assembling the multi-pass cell by placing the front mirror centered along an axis of the multi-pass cell, placing the back mirror centered along the axis and facing the front mirror, and placing a perturbing mirror having the radius of curvature at the perturbing mirror spacing from the back mirror, the perturbing mirror facing the front mirror and centered along the axis,
wherein the perturbing mirror spacing and the radius of curvature of the perturbing mirror cause the perturbing mirror to circulate the base pattern having the pattern shape according to the pattern multiplication factor.

17. The method of claim 16, wherein the perturbing mirror spacing is calculated based, at least in part, on a distance between the front mirror and the back mirror and the pattern multiplication factor.

18. The method of claim 17, wherein the perturbing mirror spacing ($S_p$) is selected as $$s_p = (d_c x_o / y_1) \sin(\pi/N_x),$$

where $x_o$ is the origin of the x-axis of a coordinate system, $y_1$ is a y-axis coordinate of an aim-in point for the beam, $c_c$ is a distance between the front mirror and the back mirror, and $N_x$ is the pattern multiplication factor.

19. The method of claim 16, wherein the radius of curvature is calculated based, at least in part, on the perturbing mirror spacing, the pattern multiplication factor, and a radius of curvature of the front mirror and the back mirror.

20. The method of claim 19, wherein the radius of curvature ($r_{cp}$) is selected as:

$$r_{cp} = s_p / [-1 + (1 + \cos(2\pi/N_x))/2(1 - s_p/r_{co})],$$

where $S_{sp}$ is the perturbing mirror spacing, $N_x$ is the pattern multiplication factor and $r_{co}$ is a radius of curvature of the front mirror and the back mirror.

* * * * *